(12) United States Patent
Askem

(10) Patent No.: US 12,029,842 B2
(45) Date of Patent: *Jul. 9, 2024

(54) SYSTEMS AND METHODS FOR DETERMINING BLOCKAGES IN A NEGATIVE PRESSURE WOUND THERAPY SYSTEM

(71) Applicant: T.J.Smith and Nephew, Limited, Hull (GB)

(72) Inventor: Ben Alan Askem, Leeds (GB)

(73) Assignee: T.J.Smith and Nephew, Limited, Hull (GB)

(*) Notice: Subject to any disclaimer, the term of this patent is extended or adjusted under 35 U.S.C. 154(b) by 0 days.

This patent is subject to a terminal disclaimer.

(21) Appl. No.: 18/224,454

(22) Filed: Jul. 20, 2023

(65) Prior Publication Data

US 2023/0355857 A1 Nov. 9, 2023

Related U.S. Application Data

(63) Continuation of application No. 17/044,535, filed as application No. PCT/EP2019/062408 on May 15, 2019, now Pat. No. 11,744,932.

(30) Foreign Application Priority Data

May 23, 2018 (GB) .................................. 1808438

(51) Int. Cl.
*A61M 1/00* (2006.01)

(52) U.S. Cl.
CPC ............... *A61M 1/75* (2021.05); *A61M 1/96* (2021.05); *A61M 1/98* (2021.05); *A61M 2205/15* (2013.01);
(Continued)

(58) Field of Classification Search
CPC ............... A61M 1/90; A61M 2205/15; A61M 2205/3331; A61M 2205/50
See application file for complete search history.

(56) References Cited

U.S. PATENT DOCUMENTS

| D239,019 S | 3/1881 | Berney |
|---|---|---|
| 4,498,850 A | 2/1985 | Perlov et al. |

(Continued)

FOREIGN PATENT DOCUMENTS

| CN | 103608049 A | 2/2014 |
|---|---|---|
| DE | 102015215165 A1 | 2/2017 |

(Continued)

OTHER PUBLICATIONS

International Preliminary Report on Patentability for Application No. PCT/EP2019/062408, mailed on Dec. 3, 2020, 8 pages.

(Continued)

*Primary Examiner* — Jessica Arble
(74) *Attorney, Agent, or Firm* — Knobbe, Martens, Olson & Bear, LLP

(57) ABSTRACT

A negative pressure wound therapy device can include a negative pressure source and a controller configured to activate the negative pressure source for a first duration of time to attempt to reduce pressure under the wound dressing to approximately ae negative pressure set point, subsequent to expiration of the first duration of time, deactivate the negative pressure source after pressure under the wound dressing is reduced to approximately the negative pressure set point, activate the negative pressure source for a second duration of time to attempt to reduce pressure in the fluid flow path, the second duration of time subsequent to the first duration of time, determine a pressure change in a fluid flow path over the second duration of time, and, in response to determining that the pressure change in the fluid flow path (Continued)

over the second duration of time indicates reduction in pressure, provide indication of a blockage.

17 Claims, 8 Drawing Sheets

(52) U.S. Cl.
CPC . *A61M 2205/3331* (2013.01); *A61M 2205/50* (2013.01)

(56) References Cited

U.S. PATENT DOCUMENTS

| | | |
|---|---|---|
| 4,731,076 A | 3/1988 | Noon et al. |
| D357,735 S | 4/1995 | McPhee |
| 5,514,088 A | 5/1996 | Zakko |
| 5,712,795 A | 1/1998 | Layman et al. |
| 6,027,490 A | 2/2000 | Radford et al. |
| 6,203,291 B1 | 3/2001 | Stemme et al. |
| 6,232,680 B1 | 5/2001 | Bae et al. |
| 6,396,407 B1 | 5/2002 | Kobayashi |
| D475,132 S | 5/2003 | Randolph |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,214,202 B1 | 5/2007 | Vogel et al. |
| D581,042 S | 11/2008 | Randolph et al. |
| D590,934 S | 4/2009 | Randolph et al. |
| D602,582 S | 10/2009 | Pidgeon et al. |
| D602,583 S | 10/2009 | Pidgeon et al. |
| D602,584 S | 10/2009 | Pidgeon et al. |
| 7,608,066 B2 | 10/2009 | Vogel |
| 7,611,500 B1 | 11/2009 | Lina et al. |
| 7,857,806 B2 | 12/2010 | Karpowicz et al. |
| 7,927,319 B2 | 4/2011 | Lawhorn |
| D645,137 S | 9/2011 | Gonzalez |
| 8,021,348 B2 | 9/2011 | Risk, Jr. et al. |
| 8,062,272 B2 | 11/2011 | Weston |
| 8,066,243 B2 | 11/2011 | Svedman et al. |
| 8,070,735 B2 | 12/2011 | Koch et al. |
| D654,164 S | 2/2012 | Cole et al. |
| D660,409 S | 5/2012 | Taggerty et al. |
| 8,215,929 B2 | 7/2012 | Shen et al. |
| 8,216,197 B2 | 7/2012 | Simmons et al. |
| 8,226,620 B2 | 7/2012 | Giezendanner et al. |
| 8,308,714 B2 | 11/2012 | Weston et al. |
| 8,317,774 B2 | 11/2012 | Adahan |
| 8,366,692 B2 | 2/2013 | Weston et al. |
| 8,409,160 B2 | 4/2013 | Locke et al. |
| 8,480,641 B2 | 7/2013 | Jacobs |
| 8,540,688 B2 | 9/2013 | Eckstein et al. |
| 8,641,693 B2 | 2/2014 | Locke et al. |
| 8,668,677 B2 | 3/2014 | Eckstein et al. |
| 8,734,425 B2 | 5/2014 | Nicolini |
| 8,858,517 B2 | 10/2014 | Pan et al. |
| 8,905,985 B2 | 12/2014 | Allen et al. |
| 9,050,398 B2 | 6/2015 | Armstrong et al. |
| 9,084,845 B2 | 7/2015 | Adie et al. |
| 9,138,531 B2 | 9/2015 | Yodfat et al. |
| 9,199,010 B2 | 12/2015 | Yao et al. |
| D750,222 S | 2/2016 | Chang |
| D750,235 S | 2/2016 | Maurice |
| D750,236 S | 2/2016 | Maurice |
| D757,260 S | 5/2016 | Lombardi, III et al. |
| 9,327,063 B2 | 5/2016 | Locke et al. |
| 9,333,281 B2 | 5/2016 | Giezendanner et al. |
| D764,047 S | 8/2016 | Bjelovuk et al. |
| D764,048 S | 8/2016 | Bjelovuk et al. |
| D764,653 S | 8/2016 | Bjelovuk et al. |
| D764,654 S | 8/2016 | Bjelovuk et al. |
| 9,415,199 B2 | 8/2016 | Tsai |
| 9,427,505 B2 | 8/2016 | Askem et al. |
| D765,830 S | 9/2016 | Bjelovuk et al. |
| 9,445,948 B2 | 9/2016 | Smola |
| D773,658 S | 12/2016 | Bow |
| 9,586,036 B2 | 3/2017 | Masuda et al. |
| D788,293 S | 5/2017 | Eckstein et al. |
| D791,939 S | 7/2017 | Turturro et al. |
| D792,586 S | 7/2017 | Becker |
| 9,737,649 B2 | 8/2017 | Begin et al. |
| D797,275 S | 9/2017 | Evans et al. |
| 9,901,664 B2 | 2/2018 | Askem |
| 9,923,401 B2 | 3/2018 | Jung |
| 10,124,093 B1 | 11/2018 | Francis et al. |
| 10,143,785 B2 | 12/2018 | Adams et al. |
| 10,155,070 B2 | 12/2018 | Childress et al. |
| D842,460 S | 3/2019 | Gierse et al. |
| D851,759 S | 6/2019 | Jones et al. |
| D852,356 S | 6/2019 | Steele et al. |
| D888,225 S | 6/2020 | Askem |
| 2002/0013545 A1 | 1/2002 | Soltanpour et al. |
| 2002/0030002 A1 | 3/2002 | Verkaart et al. |
| 2002/0098097 A1 | 7/2002 | Singh |
| 2002/0161317 A1 | 10/2002 | Risk et al. |
| 2004/0068224 A1 | 4/2004 | Couvillon, Jr. et al. |
| 2005/0234485 A1 | 10/2005 | Seegert et al. |
| 2006/0281398 A1 | 12/2006 | Yokomizo et al. |
| 2008/0234641 A1* | 9/2008 | Locke ............... A61M 1/96 604/313 |
| 2009/0216205 A1 | 8/2009 | Ryan et al. |
| 2009/0299306 A1 | 12/2009 | Buan |
| 2010/0022990 A1 | 1/2010 | Karpowicz et al. |
| 2010/0155465 A1 | 6/2010 | Mollstam et al. |
| 2010/0244780 A1 | 9/2010 | Turner et al. |
| 2011/0006876 A1 | 1/2011 | Moberg et al. |
| 2011/0060300 A1 | 3/2011 | Weig et al. |
| 2011/0076170 A1 | 3/2011 | Fujisaki et al. |
| 2011/0196291 A1 | 8/2011 | Vischer et al. |
| 2012/0078181 A1 | 3/2012 | Smith et al. |
| 2012/0109083 A1 | 5/2012 | Coulthard et al. |
| 2012/0289913 A1 | 11/2012 | Eckstein et al. |
| 2013/0012772 A1 | 1/2013 | Gunday et al. |
| 2013/0025692 A1 | 1/2013 | Heide et al. |
| 2013/0053795 A1 | 2/2013 | Coulthard et al. |
| 2013/0110058 A1* | 5/2013 | Adie ............... A61M 1/962 604/319 |
| 2013/0131616 A1 | 5/2013 | Locke |
| 2013/0237937 A1 | 9/2013 | Ramella et al. |
| 2013/0274718 A1 | 10/2013 | Yao et al. |
| 2014/0023533 A1 | 1/2014 | Ishii et al. |
| 2014/0276488 A1 | 9/2014 | Locke et al. |
| 2015/0025482 A1 | 1/2015 | Begin et al. |
| 2015/0051560 A1 | 2/2015 | Askem |
| 2015/0174320 A1 | 6/2015 | Grant et al. |
| 2015/0231021 A1 | 8/2015 | Smith et al. |
| 2015/0246164 A1 | 9/2015 | Heaton et al. |
| 2015/0320916 A1 | 11/2015 | Croteau et al. |
| 2016/0015872 A1 | 1/2016 | Luckemeyer et al. |
| 2016/0015957 A1 | 1/2016 | Tieck et al. |
| 2016/0058926 A1 | 3/2016 | Middleton et al. |
| 2016/0101278 A1 | 4/2016 | Norris et al. |
| 2016/0136339 A1 | 5/2016 | Begin et al. |
| 2016/0213843 A1 | 7/2016 | Despa et al. |
| 2016/0250398 A1 | 9/2016 | Barr et al. |
| 2016/0271305 A1 | 9/2016 | Kurihara et al. |
| 2016/0303358 A1 | 10/2016 | Croizat et al. |
| 2017/0189588 A1 | 7/2017 | Croizat et al. |
| 2017/0189666 A1 | 7/2017 | Sealfon et al. |
| 2017/0216501 A1 | 8/2017 | Armstrong et al. |
| 2017/0224975 A1 | 8/2017 | Peer et al. |
| 2017/0296716 A1 | 10/2017 | Middleton et al. |
| 2017/0319758 A1 | 11/2017 | Eddy et al. |
| 2017/0354767 A1 | 12/2017 | Carr et al. |
| 2018/0001000 A1 | 1/2018 | Herwig et al. |
| 2018/0021178 A1 | 1/2018 | Locke et al. |
| 2018/0104391 A1 | 4/2018 | Luxon et al. |
| 2018/0140466 A1 | 5/2018 | Hunt |
| 2018/0250459 A1 | 9/2018 | Kimball et al. |
| 2018/0318476 A1 | 11/2018 | Askem et al. |
| 2019/0192744 A1 | 6/2019 | Greener et al. |
| 2019/0358372 A1 | 11/2019 | Askem et al. |
| 2020/0121833 A9 | 4/2020 | Askem et al. |

(56) References Cited

U.S. PATENT DOCUMENTS

| | | | |
|---|---|---|---|
| 2020/0352818 A1 | 11/2020 | Locke et al. | |
| 2021/0077670 A1* | 3/2021 | Long | A61M 1/73 |

FOREIGN PATENT DOCUMENTS

| | | |
|---|---|---|
| EP | 0883430 B1 | 1/2007 |
| EP | 3124059 A1 | 2/2017 |
| EP | 3124060 A1 | 2/2017 |
| FR | 2939320 A1 | 6/2010 |
| GB | 1220857 A | 1/1971 |
| JP | S5647279 U | 4/1981 |
| JP | H01101978 A | 4/1989 |
| JP | H0796029 A | 4/1995 |
| JP | 2007218241 A | 8/2007 |
| JP | 6047279 B2 | 12/2016 |
| WO | WO-0061206 A1 | 10/2000 |
| WO | WO-03081762 A1 | 10/2003 |
| WO | WO-2008033788 A2 | 3/2008 |
| WO | WO-2009071924 A1 | 6/2009 |
| WO | WO-2011075706 A1 | 6/2011 |
| WO | WO-2011094410 A2 | 8/2011 |
| WO | WO-2012004298 A1 | 1/2012 |
| WO | WO-2012100624 A1 | 8/2012 |
| WO | WO-2013015827 A2 | 1/2013 |
| WO | WO-2013064852 A1 | 5/2013 |
| WO | WO-2013078214 A1 | 5/2013 |
| WO | WO-2014115819 A1 | 7/2014 |
| WO | WO-2014164655 A1 | 10/2014 |
| WO | WO-2015197462 A1 | 12/2015 |
| WO | WO-2016103031 A1 | 6/2016 |
| WO | WO-2016109041 A1 | 7/2016 |
| WO | WO-2016109048 A1 | 7/2016 |
| WO | WO-2017044138 A1 | 3/2017 |
| WO | WO-2017062042 A1 | 4/2017 |
| WO | WO-2017160412 A1 | 9/2017 |
| WO | WO-2017197357 A4 | 1/2018 |
| WO | WO-2018009873 A1 | 1/2018 |
| WO | WO-2018009880 A1 | 1/2018 |
| WO | WO-2018041854 A1 | 3/2018 |
| WO | WO-2018150263 A1 | 8/2018 |
| WO | WO-2018150267 A2 | 8/2018 |
| WO | WO-2018167199 A1 | 9/2018 |
| WO | WO-2018185101 A1 | 10/2018 |
| WO | WO-2018195101 A1 | 10/2018 |
| WO | WO-2019063467 A1 | 4/2019 |
| WO | WO-2019129581 A2 | 7/2019 |
| WO | WO-2019139829 A1 | 7/2019 |
| WO | WO-2019179943 A1 | 9/2019 |
| WO | WO-2019211730 A1 | 11/2019 |
| WO | WO-2019211731 A1 | 11/2019 |
| WO | WO-2019211732 A1 | 11/2019 |
| WO | WO-2019224059 A1 | 11/2019 |
| WO | WO-2020011690 A1 | 1/2020 |

OTHER PUBLICATIONS

International Search Report and Written Opinion for Application No. PCT/EP2019/062408, mailed on Jul. 31, 2019, 9 pages.
Jenkins R.W., et al., "Mechanisms of Resistance to Immune Checkpoint Inhibitors," British Journal of Cancer, Jan. 2, 2018, vol. 118, https://doi.org/10.1038/bjc.2017.434, pp. 9-16.
Wikipedia, "Battery Charger," retrieved from https://web.archive.org/web/20181109005000/https://en.wikipedia.org/wiki/Battery_charger, on Nov. 9, 2018, 12 pages.

* cited by examiner

SYSTEMS AND METHODS FOR DETERMINING BLOCKAGES IN A NEGATIVE PRESSURE WOUND THERAPY SYSTEM

CROSS-REFERENCE TO RELATED APPLICATIONS

This application is a continuation of U.S. application Ser. No. 17/044,535, filed Oct. 1, 2020, which is a U.S. national stage application of International Patent Application No. PCT/EP2019/062408, filed May 15, 2019, which claims the benefit of GB Application No. 1808438.4, filed May 23, 2018.

FIELD

Embodiments or arrangements disclosed herein relate to methods and apparatuses for dressing and treating a wound with topical negative pressure (TNP) therapy. For example, but without limitation, any embodiments disclosed herein may relate to treating a wound with negative pressure. As another non-limiting example, any embodiments disclosed herein relate to apparatuses and methods for controlling the operation of a TNP system.

DESCRIPTION OF THE RELATED ART

Many different types of wound dressings are known for aiding in the healing process of a human or animal. These different types of wound dressings include many different types of materials and layers, for example, pads such as gauze pads or foam pads. Topical negative pressure ("TNP") therapy, sometimes referred to as vacuum assisted closure, negative pressure wound therapy, or negative pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue edema; encouraging blood flow; stimulating the formation of granulation tissue; removing excess exudates, and may reduce bacterial load and thus reduce the potential for infection of the wound. Furthermore, TNP therapy permits less outside disturbance of the wound and promotes more rapid healing.

SUMMARY

Embodiments disclosed herein are directed to a reduced pressure appliance and methods of treatment using a reduced pressure appliance, and may be useful in the treatment of wounds using reduced pressure.

In some embodiments, a negative pressure wound therapy apparatus can include a negative pressure source that can be configured to provide negative pressure via a fluid flow path to a wound covered by a wound dressing. The negative pressure source can be further configured to be periodically activated to reduce pressure under the wound dressing to approximately a negative pressure set point and be periodically deactivated after the pressure under the wound dressing is reduced to the approximately negative pressure set point. The apparatus can include a controller that can be configured to activate the negative pressure source for a first duration of time to attempt to reduce the pressure to approximately the negative pressure set point. Subsequent, to the expiration of the first duration of time, the controller can deactivate the negative pressure source after the pressure under the wound dressing is reduced to approximately the negative pressure set point. The controller can distinguish between a blockage in the fluid flow path and the presence of a low leak in the fluid flow path. The controller can activate the negative pressure source for a second duration of time in an attempt to reduce pressure in the fluid flow path. The second duration of time can be subsequent to the first duration of time. The controller can deactivate the negative pressure source subsequent to expiration of the second duration of time. The controller can determine a pressure change in the fluid flow path over at least part of the second duration of time, and in response to determining that the pressure change in the fluid flow path over the at least part of the second duration of time indicates reduction in pressure, provide indication of blockage in the fluid flow path.

The apparatus of the preceding paragraph can include one or more of the following features. The low leak can corresponds to a leak rate of gas entering the fluid flow path from external environment at which the apparatus is configured to provide or maintain negative pressure wound therapy. The controller can be further configured to, in response to determining that the pressure change in the fluid flow path over the at least part of the second duration of time does not indicate reduction in pressure, provide indication that the low leak is present in the fluid flow path. The second duration time can be shorter than the first duration of time over which the negative pressure source is activated to attempt to reduce pressure under the wound dressing to approximately the negative pressure set point. The pressure in the fluid flow path can be reduced over the second duration of time when the negative pressure source is active due to evacuation of gas from a portion of the fluid flow path downstream from the blockage. The fluid flow path can include a leak, and the portion of the fluid flow path downstream from the blockage can be depressurized over a duration of time when the negative pressure source is deactivated due to the leak. The apparatus can further include a pressure sensor configured to measure pressure in the fluid flow path. The controller can be further configured to determine the pressure change in the fluid flow path over the at least part of the second duration of time based on a difference between a first pressure measurement made by the pressure sensor approximately at a start of the second duration of time and a second pressure measurement made by the pressure sensor approximately at an end of the second duration of time. The apparatus can further include a canister configured to be fluidically connected to the negative pressure source and to store at least some fluid removed from the wound.

In some implementations, a negative pressure wound therapy apparatus can include a negative pressure source configured to provide negative pressure via a fluid flow path to a wound covered by a wound dressing, the negative pressure source further configured to be periodically activated to reduce pressure under the wound dressing to approximately a negative pressure set point and be periodically deactivated after pressure under the wound dressing is reduced to approximately the negative pressure set point. The apparatus can also include a controller configured to indicate a blockage in the fluid flowpath. The controller can activate the negative pressure source for a first duration of time to attempt to reduce pressure under the wound dressing to approximately the negative pressure set point. Subsequent to expiration of the first duration of time, the controller can deactivate the negative pressure source after pressure under the wound dressing is reduced to approximately the negative pressure set point. The controller can activate the negative pressure source for a second duration of time to attempt to reduce pressure in the fluid flow path, the second duration of time subsequent to the first duration of time. The controller can deactivate the negative pressure source subsequent to expiration of the second duration of time. The controller can determine a pressure change in the fluid flow path over the at least part of the second duration of time. In response to determining that the pressure change in the fluid flow path over the at least part of the second duration of time indicates reduction in pressure, the controller can provide indication of the blockage in the fluid flow path.

The apparatus of any of the preceding paragraphs can include one or more of the following features. The second duration time can be shorter than the first duration of time over which the negative pressure source is activated to attempt to reduce pressure under the wound dressing to approximately the negative pressure set point. The pressure in the fluid flow path can be reduced over the at least part of the duration of time when the negative pressure source is active due to evacuation of gas from a portion of the fluid flow path downstream from the blockage. The fluid flow path can include a leak and the portion of the fluid flow path downstream from the blockage can be depressurized over another duration of time when the negative pressure source is deactivated due to the leak. The apparatus can further include a pressure sensor configured to measure pressure in the fluid flow path. The controller can be further configured to determine the pressure change in the fluid flow path over the at least part of the duration of time based on a difference between a first pressure measurement made by the pressure sensor approximately at a start of the duration of time and a second pressure measurement made by the pressure sensor approximately at an end of the duration of time. The apparatus can further include a canister configured to be fluidically connected to the negative pressure source and to store at least some fluid removed from the wound.

In some implementations, a negative pressure wound therapy apparatus can include a negative pressure source configured to provide negative pressure via a fluid flow path to a wound covered by a wound dressing, the negative pressure source further configured to be periodically activated to reduce pressure under the wound dressing to approximately a negative pressure set point and be periodically deactivated after pressure under the wound dressing is reduced to approximately the negative pressure set point. The apparatus can also include a controller configured to activate the negative pressure source for a duration of time to attempt to reduce pressure in the fluid flow path. The controller can deactivate the negative pressure source subsequent to expiration of the duration of time. The controller can determine a pressure change in the fluid flow path over at least part of the duration of time, and in response to determining that the pressure change in the fluid flow path over the at least part of the duration of time indicates reduction in pressure, provide indication of the blockage in the fluid flow path.

The apparatus of any of the preceding paragraphs can include one or more of the following features. The pressure in the fluid flow path can be reduced over the at least part of the duration of time when the negative pressure source is active due to evacuation of gas from a portion of the fluid flow path downstream from the blockage. The fluid flow path can include a leak, and a portion of the fluid flow path downstream from the blockage can be depressurized over another duration of time when the negative pressure source is deactivated due to the leak. The apparatus can further include a pressure sensor configured to measure pressure in the fluid flow path. The controller can further be configured to determine the pressure change in the fluid flow path over the at least part of the duration of time based on a difference between a first pressure measurement made by the pressure sensor approximately at a start of the duration of time and a second pressure measurement made by the pressure sensor approximately at an end of the duration of time. The apparatus can further include a canister configured to be fluidically connected to the negative pressure source and to store at least some fluid removed from the wound.

In some implementations, a method of operating a negative pressure wound therapy apparatus including a negative pressure source and a controller can include, by the controller, indicating a blockage in a fluid flowpath that can be fluidically connect a wound covered by a wound dressing to the negative pressure source configured to provide negative pressure to the wound. The method can include activating the negative pressure source for a first duration of time to attempt to reduce pressure under the wound dressing to approximately the negative pressure set point. The method can further include subsequent to expiration of the first duration of time, deactivating the negative pressure source after pressure under the wound dressing is reduced to approximately the negative pressure set point. The method can further include activating the negative pressure source for a second duration of time to attempt to reduce pressure in the fluid flow path, the second duration of time subsequent to the first duration of time. The method can further include deactivating the negative pressure source subsequent to expiration of the second duration of time. The method can further include determining a pressure change in the fluid flow path over at least part of the second duration of time. The method can further include in response to determining that the pressure change in the fluid flow path over at least part of the second duration of time indicates reduction in pressure, provide indication of the blockage in the fluid flow path.

The method of the preceding paragraph can include one or more of the following features. The second duration time can be shorter than the first duration of time over which the negative pressure source is activated to attempt to reduce pressure under the wound dressing to approximately the negative pressure set point. The pressure in the fluid flow path can be reduced over the at least part of the second duration of time when the negative pressure source is active due to evacuation of gas from a portion of the fluid flow path downstream from the blockage. The fluid flow path can include a leak, and the portion of the fluid flow path downstream from the blockage can be depressurized over a duration of time when the negative pressure source is deactivated due to the leak. The method can include measuring pressure in the fluid flow path using a pressure sensor and determining the pressure change in the fluid flow path over at least part of the second duration of time based on a difference between a first pressure measurement made by the pressure sensor approximately at a start of the second duration of time and a second pressure measurement made by the pressure sensor approximately at an end of the second duration of time.

BRIEF DESCRIPTION OF THE DRAWINGS

Features and advantages of the present disclosure will be apparent from the following detailed description, taken in conjunction with the accompanying drawings of which.

DETAILED DESCRIPTION

Figure 1:
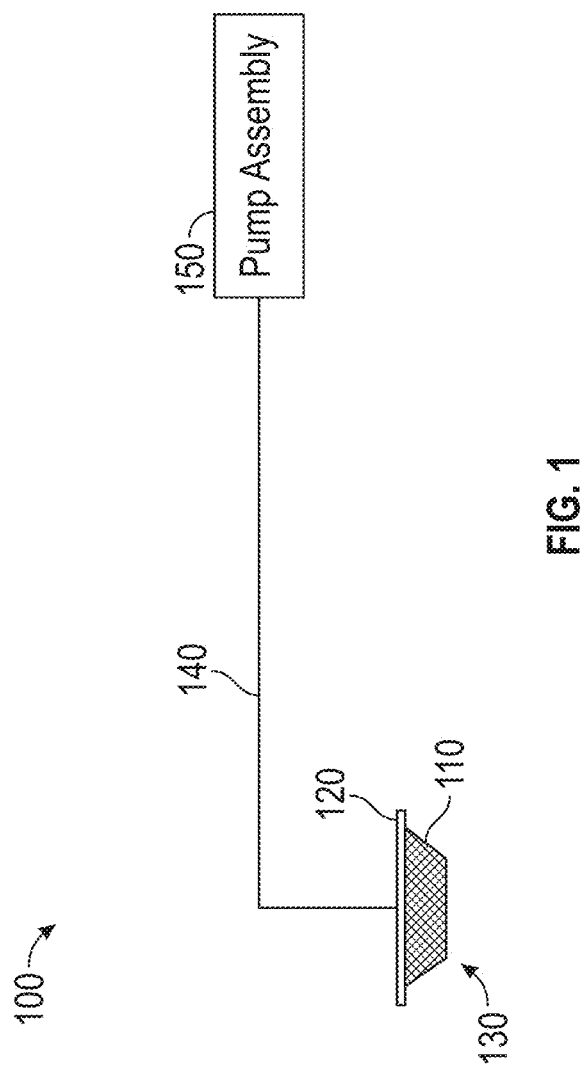
FIG. 1 illustrates a negative pressure wound therapy system including a pump assembly according to some embodiments.

The present disclosure relates to methods and apparatuses for dressing and treating a wound with reduced pressure therapy or topical negative pressure (TNP) therapy. In particular, but without limitation, embodiments of this disclosure relate to negative pressure therapy apparatuses, methods for controlling the operation of TNP systems, and methods of using TNP systems. The methods and apparatuses can incorporate or implement any combination of the features described below.

Many different types of wound dressings are known for aiding in the healing process of a human or animal. These different types of wound dressings include many different types of materials and layers, for example, gauze, pads, foam pads or multi-layer wound dressings. TNP therapy, sometimes referred to as vacuum assisted closure, negative pressure wound therapy, or reduced pressure wound therapy, can be a beneficial mechanism for improving the healing rate of a wound. Such therapy is applicable to a broad range of wounds such as incisional wounds, open wounds and abdominal wounds or the like.

TNP therapy can assist in the closure and healing of wounds by reducing tissue edema, encouraging blood flow, stimulating the formation of granulation tissue, removing excess exudates, and reducing bacterial load and thus, infection to the wound. Furthermore, TNP therapy can permit less outside disturbance of the wound and promote more rapid healing.

As is used herein, reduced or negative pressure levels, such as −X mmHg, represent pressure levels that are below atmospheric pressure, which typically corresponds to 760 mmHg (or 1 atm, 29.93 inHg, 101.325 kPa, 14.696 psi, etc.). Accordingly, a negative pressure value of −X mmHg reflects pressure that is X mmHg below atmospheric pressure, such as a pressure of (760−X) mmHg. In addition, negative pressure that is "less" or "smaller" than −X mmHg corresponds to pressure that is closer to atmospheric pressure (for example, −40 mmHg is less than −60 mmHg). Negative pressure that is "more" or "greater" than −X mmHg corresponds to pressure that is further from atmospheric pressure (for example, −80 mmHg is more than −60 mmHg).

Overview

Embodiments disclosed in this section or elsewhere in this specification relate to apparatuses and methods of treating a wound with reduced pressure, including pump and wound dressing components and apparatuses. The apparatuses and components comprising the wound overlay and packing materials, if any, are sometimes collectively referred to in this section or elsewhere in this specification as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, electrical burns, diabetic ulcers, pressure ulcers, stoma, surgical wounds, trauma and venous ulcers or the like.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue edema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. TNP therapy can help to stabilize the tissue in the apposed position of closure. A further beneficial use of TNP therapy can be found in grafts and flaps where removal of excess fluid is important and close proximity of the graft to tissue is required in order to ensure tissue viability.

Negative Wound Pressure Therapy System

FIG. 1 illustrates a negative or reduced pressure wound treatment system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a reduced pressure wound therapy assembly 150 configured to supply reduced pressure. The wound cover 120 can be in fluidic communication with the wound cavity 110. The assembly 150 can be a canisterless assembly (meaning that exudate is collected in the wound dressing or is transferred via tube 140 for collection to another location). However, any of the assemblies disclosed herein can be configured to include or support a canister. Additionally, in any of the systems disclosed herein, any of the assemblies can be mounted to or supported by the dressing, or adjacent to the dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

The wound cover 120 can have a port (not shown) configured to receive an end of the conduit 140. The port can be Renays Soft Port available from Smith & Nephew. The conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the assembly 150 and the wound cover 120, so as to supply the reduced pressure provided by the assembly 150 to wound cavity 110.

The wound cover 120 and the wound filler 130 can be provided as a single article or an integrated single unit. No wound filler can also be possible and the wound cover by itself can be considered the wound dressing. The wound dressing can then be connected, via the conduit 140, to a source of negative pressure, such as the assembly 150. The assembly 150 can be miniaturized and portable, although larger conventional negative pressure sources can also be used.

The wound cover 120 can be located over a wound site to be treated. The wound cover 120 can form a substantially sealed cavity or enclosure over the wound site. The wound cover 120 can be configured to have a film having a high water vapor permeability to enable the evaporation of surplus fluid, and can have a super absorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

The system can be designed to operate without the use of an exudate canister. The system can be configured to support an exudate canister. Configuring the assembly 150 and tubing 140 can be done so that the tubing 140 can be quickly and easily removed from the assembly 150 can facilitate or improve the process of dressing or assembly changes, if necessary. The system can be configured to have any suitable connection between the tubing and the assembly 150.

The assembly 150 can be configured to deliver negative pressure of approximately −80 mmHg, or between about −20 mmHg and 200 mmHg. The pressure range can be between about −40 mmHg and −150 mmHg. Alternatively, a pressure range of up to −75 mmHg, up to −80 mmHg or over −80 mmHg can be used. Also a pressure range of below −75 mmHg can be used. Alternatively, a pressure range of over approximately −100 mmHg, or even 150 mmHg, can be supplied by the assembly 150.

In operation, the wound filler 130 is inserted into the wound cavity 110 and wound cover 120 is placed so as to seal the wound cavity 110. The assembly 150 provides a source of a negative pressure to the wound cover 120, which is transmitted to the wound cavity 110 via the wound filler 130. Fluid (e.g., wound exudate) is drawn through the conduit 140, and can be stored in a canister. Fluid can be absorbed by the wound filler 130 or one or more absorbent layers (not shown).

Wound dressings that may be utilized with the assembly and other embodiments of the present application include Renasys-F, Renasys-G, Renasys AB, and Pico Dressings available from Smith & Nephew. Further description of such wound dressings and other components of a negative pressure wound therapy system that may be used with the assembly and other embodiments of the present application are found in U.S. Patent Publication Nos. 2011/0213287, 2011/0282309, 2012/0116334, 2012/0136325, and 2013/0110058, each of which is incorporated by reference in its entirety. Other suitable wound dressings can be utilized.

Figure 2A:
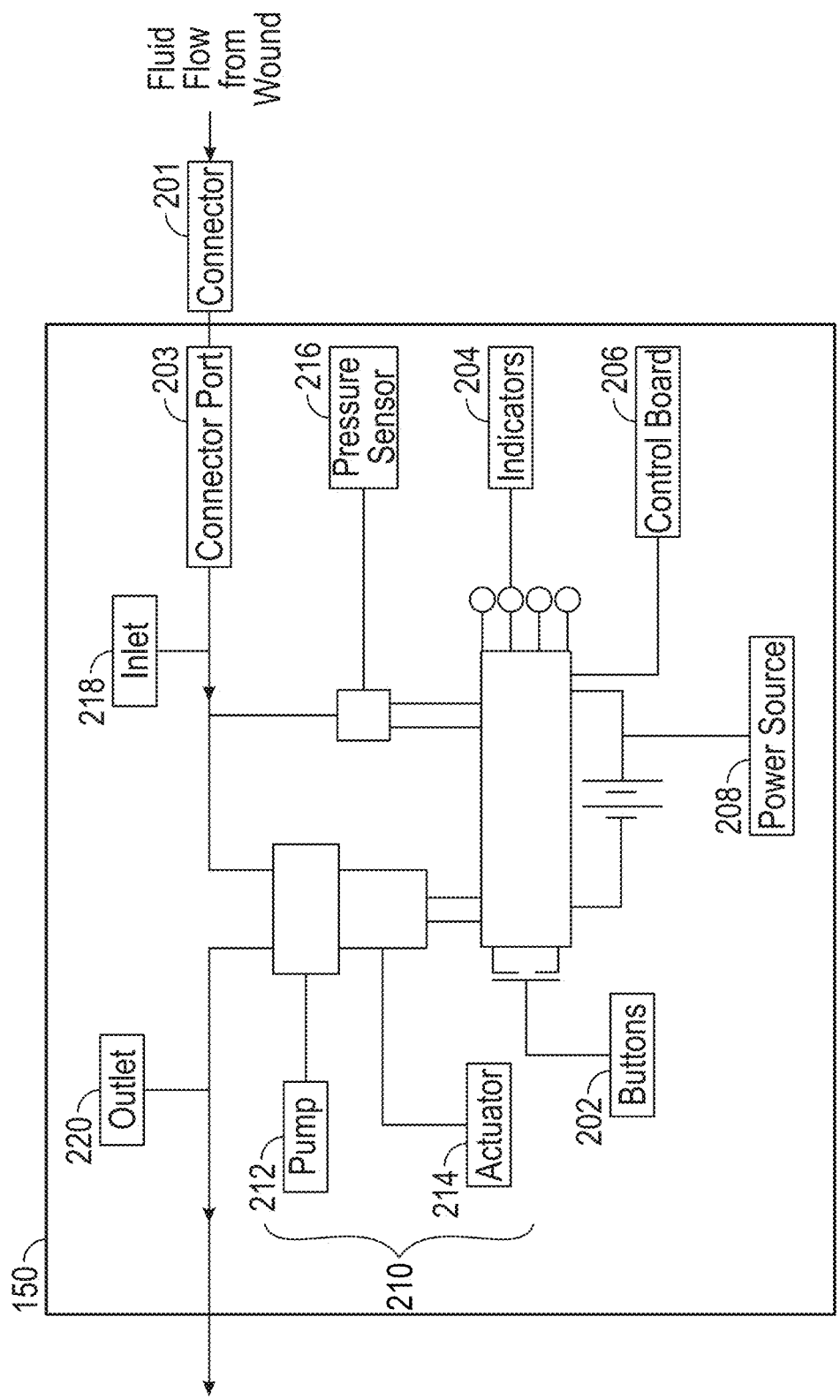
FIG. 2A illustrates a dual mode negative pressure wound therapy system operating in a canisterless mode of operation according to some embodiments.
Figure 2B:
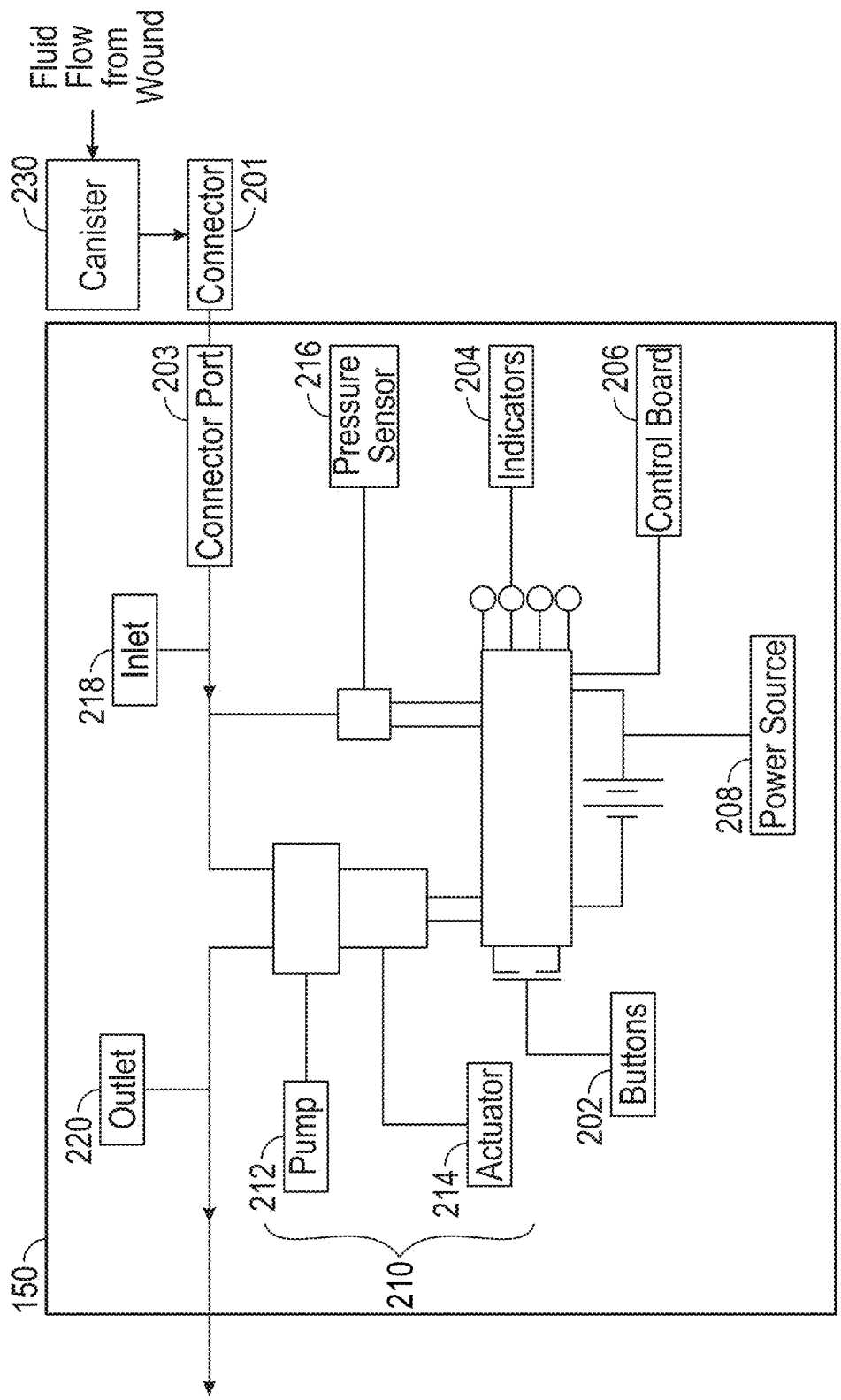
FIG. 2B illustrates a dual mode negative pressure wound therapy system operating in a canister mode of operation according to some embodiments.

FIGS. 2A-2B illustrate that the reduced pressure wound therapy system can be configured to operate with and without a canister (for example, in canister and canisterless modes) according to some embodiments. FIG. 2A shows a TNP system 200A that has a wound dressing connected directly to the pump assembly 150 (for example, canisterless mode). FIG. 2B shows a TNP system 200B that has a canister 230 interposed between the wound dressing and the pump assembly 150 (for example, canister mode). At the beginning of the application of negative pressure wound therapy to a wound when the wound is in the early stages of the healing process and exudes a significant volume of exudate, the reduced pressure wound therapy system can operate with a canister. In this mode of operation, the negative pressure wound therapy system can operate with a foam or gauze RENASYS™ dressing sold by Smith & Nephew or any other suitable dressing. Operation of the reduced pressure wound therapy system with a canister can sometimes be referred to herein as "RENASYS", "RENASYS-mode", or derivatives thereof. As the wound is progressing through the healing process and is starting to exude a smaller volume of exudate, the canister can be removed and the negative pressure wound therapy system may operate with an absorbent dressing, such as the PICO™ dressing sold by Smith & Nephew or any other suitable dressing that retains the wound exudate within the dressing. Operation of the reduced pressure wound therapy system without a canister may sometimes be referred to herein as "PICO", "PICO-mode", or derivatives thereof.

The pump assembly 150 can include one or more switches or buttons 202, one or more indicators 204, and a control board 206, which can include one or more controllers, one or more memories, or the like. The one or more buttons 202 and the one or more indicators 204 (which collectively make up a user interface) can be in electrical communication with the control board 206, which can include one or more controllers and memory. The one or more buttons 202 can be used for any suitable purpose for controlling an operation of the pump assembly 150. For example, the one or more buttons 202 can be used to activate the pump system 150, pause the pump assembly 150, and clear system indicators such as one or more of the one or more indications 204. The one or more buttons 202 can by any type of switch or button, such as a touchpad, touch screen, keyboard, and so on. One or more buttons 202 can be a press button. One or more buttons 202 can be included on a touchscreen interface.

The pump assembly 150 can include a connector port 203 adapted to receive a connector 201. The connector 201 can be a part of the canister or the wound dressing that is attached to the pump assembly 150, as described herein. The connector 201 can be removably attached to the connector port 203. In some arrangements, a first connector 201 can be removed from the pump assembly 150 and replaced with a second connector 201 that is then attached to the pump assembly 150. For example, a first connector 201 that is connected to a RENASYS™ dressing can be removed from the connector port 203 and replaced with a second connector 201 that connected to a PICO™ dressing, thereby allowing the pump assembly 150 to be switched from canister to a canisterless mode of operation. As described in more detail below, the connector 201 and/or pump assembly 150 can be adapted to allow the pump assembly 150 to detect whether a canister or canisterless connector 201 is attached to the connector port 203. In some arrangements, the operation of the pump assembly 150 can be adjusted according to whether the pump assembly 150 detects a canister or a canisterless connector 201 is connected to the connector port 203.

The connector port 203 can include one or more connector switches in electrical communication with the control board 206, which can include one or more controllers. The one or more connector switches can be configured to engage one or more connectors of the canister or the dressing. One or more connector switches can advantageously permit the pump assembly 150 (e.g., the control board 206) to differentiate between a canister connection and a dressing connection. One or more of the connectors 201 can include one or more connector switches in addition to or in lieu of the one or more connector switches of the connector port 203. The connector switches contemplated herein can be mechanical, electrical, optical, and/or magnetic, or any other suitable switch, and can include sensors and the like. The connector switches can be configured to close or open an electrical circuit, thereby permitting the control board 206 to detect whether the connector switch is engaged or disengaged. For example, as described in more detail below, the connector port 203 can include a connector switch that is actuated by a portion of a connector 201 that couples a canister to the connector port 203. The connector switch can be further configured so that the switch is not actuated by a connector 201 that couples a dressing to the connector port 203, thereby allowing the control board 206 to detect whether a canister or a dressing is attached to the connector port 203. In some arrangements, the pump assembly 150 can be configured so that the connector switch is activated by a connector 201 that couples a dressing to the connector port 203 and is not activated by a connector 201 that couples a canister to the connector port 203.

With continued reference to FIG. 2A, the one or more indicators 204 can indicate one or more operating or failure conditions of the pump assembly 150. Each of the one or more indicators 204 can provide an indication regarding a different operating or failure condition. An active (such as, lit) visual indicator (such as, LED) of the one or more indicators 204 can represent a certain operation condition for the pump assembly 150. For example, a dressing indicator of the one or more indicators 204 can provide an indication as to presence of leakages or leaks in the TNP system 100, and an active dressing indicator can represent a leak. As another example, a dressing capacity indicator of the one or more indicators 204 can provide an indication as to the remaining fluid capacity of the wound dressing or canister, and an active dressing capacity indicator can represent that the wound dressing or canister is at or nearing capacity. As yet another example, a power source indicator of the one or more indicators 204 can provide an indication as to remaining capacity or life of the power source 208, such as one or more batteries, and an active power source indicator can represent a low capacity. One or more indicators 204 can represent a combination of one or more of the above operating or failure conditions of the pump assembly 150 or other operating or failure conditions for the pump assembly 150.

The one or more indicators 204 can be icons. For example, the one or more indicators 204 can be activated (e.g., lit) via an illumination source such as LEDs (not shown) of pump assembly 150. The one or more indicators 204 can, for instance, be of a different color, two different colors (e.g., two indicators can share the same color), or same color. The pump assembly 150 can include visual, audible, tactile, haptic, or other types of indicators or alarms configured to signal to the user various operating conditions. Such conditions include system on/off, standby, pause, normal operation, dressing problem, leak, error, and the like. The indicators can include speakers, displays, light sources, etc., or combinations thereof. One or more buttons indicators 204 can be included on a touchscreen interface.

The pump assembly 150 can be powered by a power source 208 such as a one or more battery cells or any other suitable power source. Battery cells can include any combination of one or more of lithium-ion, lithium-polymer, lithium iron phosphate, lead acid, nickel based, alkaline, or the like. The pump assembly 150 can also include a source of negative pressure 210, which can include a pump 212 powered by an actuator 214, such as an electric motor. The actuator 214 can be integrated into the pump 212. The negative pressure source 210 can be a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, a pump operated by a voice coil actuator, or any other suitable pump or micropump or any combinations of the foregoing, The pump assembly 150 can also include one or more pressure sensors 216 that measure pressure in the fluid flow path. The power source 208 can supply power to electro-mechanical components of the pump assembly 150, including one or more of the negative pressure source 210, pressure sensor 216, control board 206, buttons 202, and indicators 204.

The pump assembly 150 can further include an inlet 218 to connect the pump assembly 150 to the wound dressing. For example, the inlet 218 can be connected to the connector port 203 and the connector 201 that is in fluid communication with the wound dressing via a fluid flow path.

The pump assembly 150 can also include an outlet 220. The outlet 220 can vent or exhaust gas to the atmosphere. A filter (not shown) can be interposed between the outlet 220 and the atmosphere. The filter can provide filtration of the gas prior to venting the gas to the atmosphere. The filter can be a bacterial filter, odor filter, or any combination thereof. A dampening component (not shown), such as a noise dampening component, can be interposed between the outlet 220 and the atmosphere. The dampening component can reduce the noise generated by the pump assembly 150 during operation. The pump assembly 150 can communicate information, such as information related to provision of negative pressure therapy, to one or more remote devices. Such communication can be performed using a wired or wireless interface.

FIG. 2B illustrates the pump assembly 150 of FIG. 2A with a canister 230 additionally positioned in a fluid flow path between the inlet 218 and the wound dressing. The connector 201 can fluidically connect the canister 230 to the connector port 203. As discussed further below, the connector 201 can be configured to signal to the pump assembly 150 whether the connector port 203 is connected to a wound dressing directly or whether a canister 230 is disposed between the connector 203 and the wound dressing.

The control board 206 (for example, a controller) adjusts one or more operational parameters of negative pressure wound therapy depending on whether the pump assembly is connected to the canister or the dressing. For example, in canisterless mode, the level of negative pressure provided to the wound can be reduced compared to canister mode because the wound is exuding a smaller amount of fluid. As another example, detection of one or more operating conditions can be enabled, disabled, or adjusted. For instance, in canisterless mode, canister full detection (or blockage detection) and alarming can be disabled and, instead, dressing full detection and alarming can be enabled.

The pump assembly 150 includes a user interface, such as one or more displays, indicators, lights, buttons, switches, speakers, vibrating elements, etc. The user interface can be adjusted based on detection of a canister. For example, in canister mode, the user interface can include an indicator alerting a user when canister becomes full. In canisterless mode, this indicator can be replaced with an indicator alerting the user when the dressing become full. The indicators can be icons.

Figure 3A:
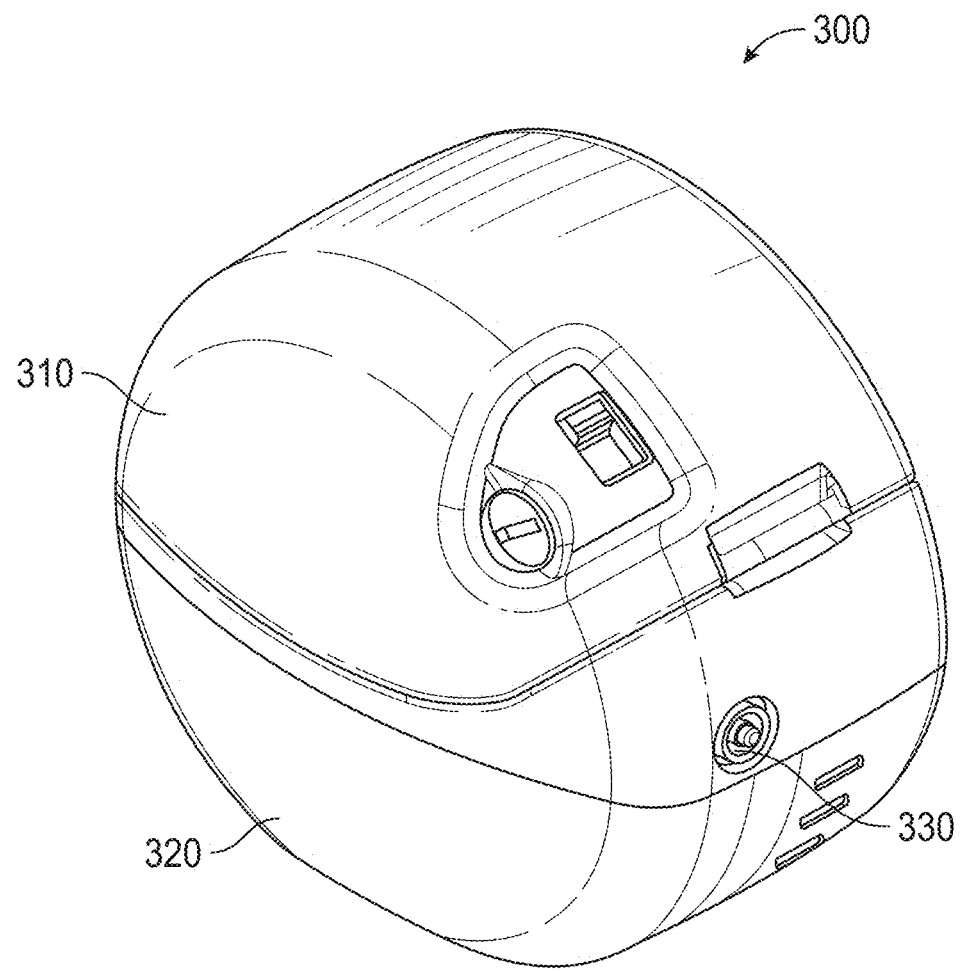
FIGS. 3A and 3B illustrate a dual mode negative pressure wound therapy apparatus according to some embodiments.

FIG. 3A depicts a perspective view 300 of a dual mode TNP system in a canister mode according to some embodiments. In the illustrated system, a canister 320 is attached to a pump assembly 310 (which can be similar as the pump assembly 150 described herein). The pump assembly 310 can be adapted to be slidably coupled to the canister 320. The canister 320 can have an inlet 330 through which wound exudate can enter the canister 320. The pump assembly 310 can slide back to disengage the pump assembly 310 from the canister 320, as illustrated with respect to FIG. 3B.

Figure 3B:
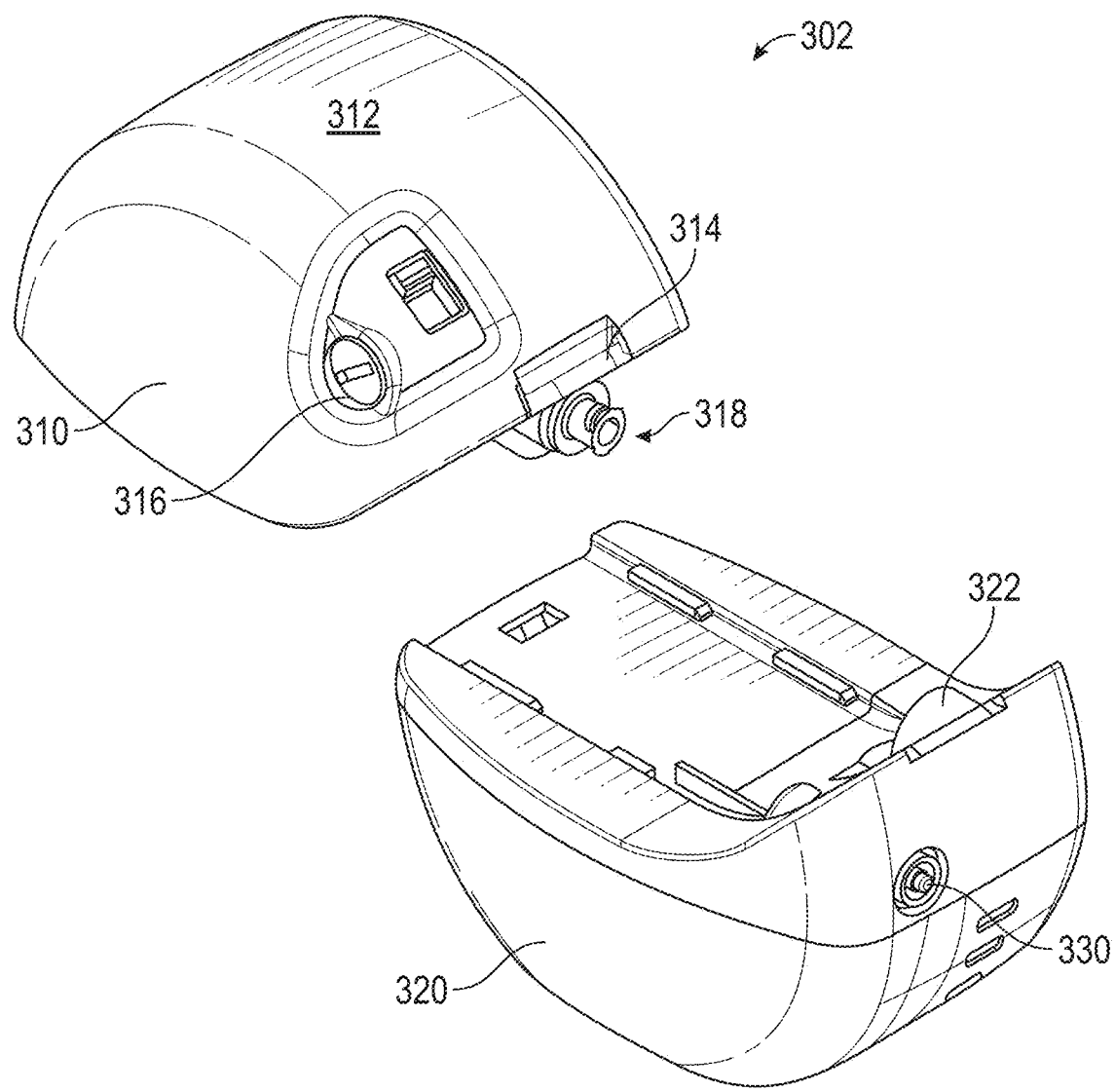

FIG. 3B depicts a perspective view 302 of the TNP system of FIG. 3A with the canister 320 disengaged from the pump assembly 310. In some cases, the pump assembly 310 can operate in a canisterless mode. As described above, the pump assembly 310 can have a connector port 318 that is adapted to connect to a connector 201 (shown schematically in FIGS. 2A-2B). The connector 201 can be a canister connector or a canisterless connector as discussed herein. The connector port 318 can be fluidically connected to a negative pressure source (such as, vacuum pump) housed within the pump assembly 310. The connector port 318 can establish a flow path between the negative pressure source of the pump assembly 310 and the connector 201 that is connected to the connector port 318. The pump assembly 310 can provide negative pressure to a canister connector 322 or a canisterless connector that is attached to the connector port 318. The canister 320 can have the canister connector 322 that fluidically connects to the connector port 318 when the pump assembly 310 is slidably mounted onto the canister 320. Mounting (such as slidingly mounting) the canister 320 can activate a switch configured to indicate that the canister has been connected, as described herein. Conversely, dismounting of the canister 320 can deactivate the switch. The canister 320 can have an inlet 330 through which wound exudate enters the canister 320 when negative pressure is applied to the canister 320 through the canister connector 322.

With continued reference to FIGS. 3A-3B, the pump assembly 310 can include a dial 316 (also illustrated in FIGS. 4A-4B) that allows pressure selection on the pump assembly 310. The magnitude of the negative pressure supplied by the pump assembly 310 can be adjusted by turning the dial 316. The dial 316 can be adapted to turn to two or more discreet settings. For example, the dial 316 can have three discreet settings that allow the negative pressure provided by the pump assembly 310 to be set to one of three settings (e.g., −60 mmHg, −80 mmHg, and −120 mmHg). The pump assembly 310 can include a bar 314 that can be used as an anchoring site for a strap or clasp, thereby allowing the pump assembly 310 to be suspended from a strap that is attached to the bar 314. When the canister 320 and the pump assembly 310 are connected together, a ramped portion of the top surface of the canister 320 can form an overhang that is supported on an inclined portion of the bottom surface of the pump assembly 310, thereby enhancing retention of the canister 320 on the pump assembly 310 when the pump assembly 310 is suspended from the bar 314. The pump assembly 310 can include one or more icons on the housing 312 of the pump assembly 310. The icons can be backlit by a light source that is disposed within the housing 312 of the pump assembly 310.

Figure 4A:
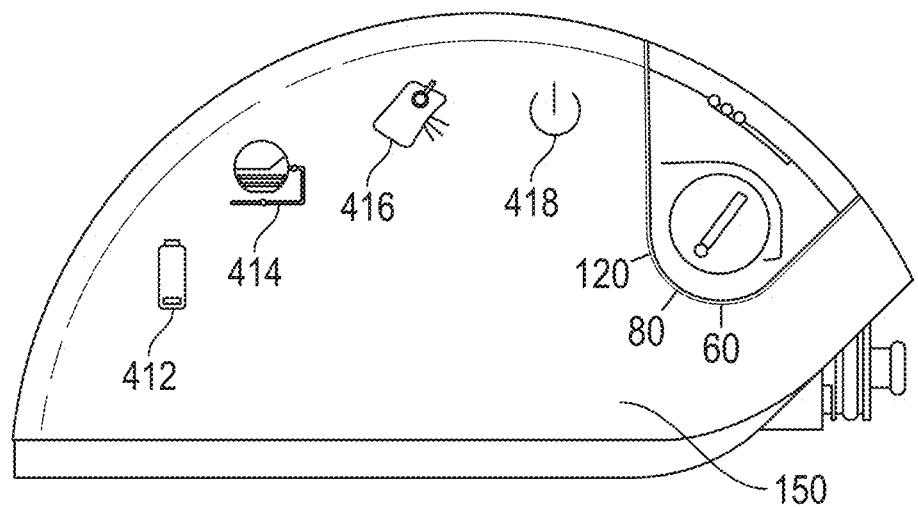
FIGS. 4A and 4B illustrate a dual mode negative pressure wound therapy apparatus according to some embodiments.
Figure 4B:
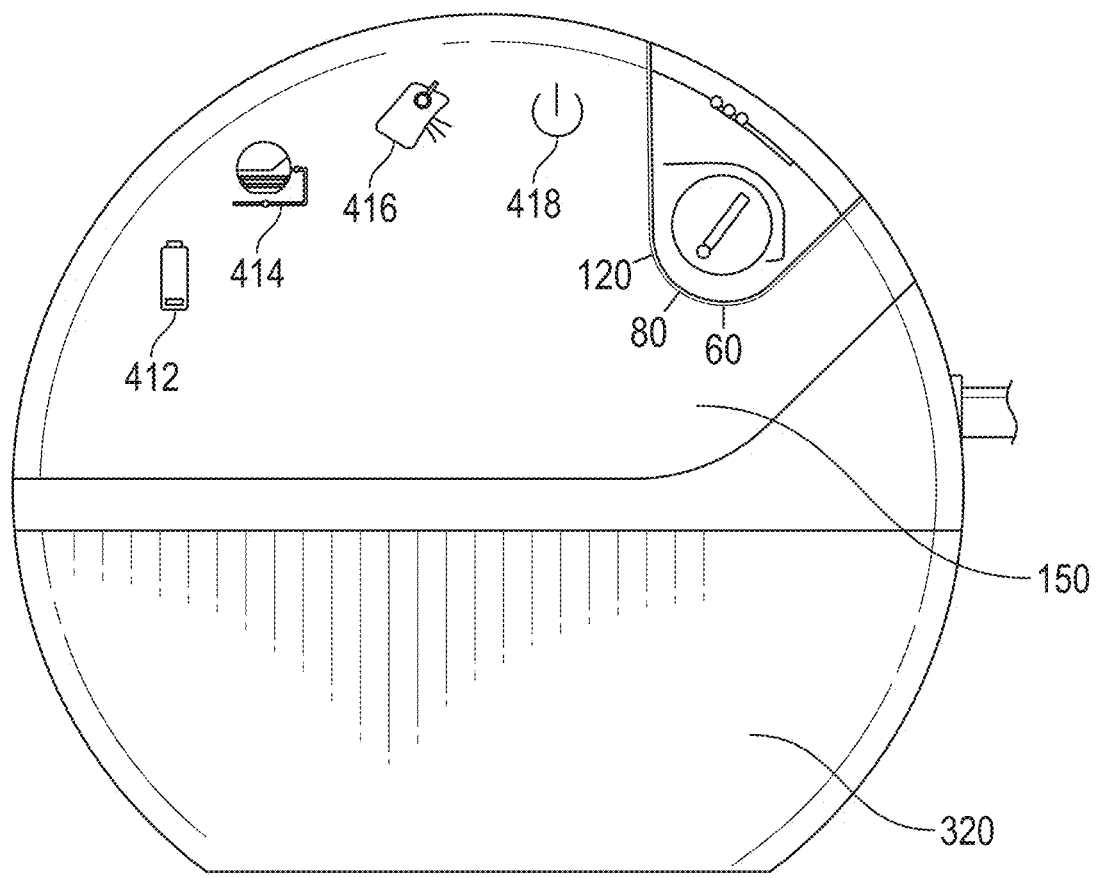

FIGS. 4A and 4B illustrate various visual indicators on a housing of any of the pump assemblies described herein, such as the pump assembly 150, including 412 (battery level), 414 (blockage in fluid flow path), 416 (leak in fluid flow path), and 418 (provision of therapy) in canisterless (FIG. 4A) and canister (FIG. 4B) modes of operation. FIG. 4B also illustrates the pump assembly 150 connected to a canister 160. The illustrated indicators can be configured to provide various indications as described herein. For example, certain indications can include non-critical alarms that do not result in pausing therapy, while certain indications are critical alarms that result in pausing therapy. For instance, as described herein, detection of a minor or sustainable air leak does not result in pausing therapy, whereas detection of a major or unsustainable air leak results in pausing therapy.

Figure 5:
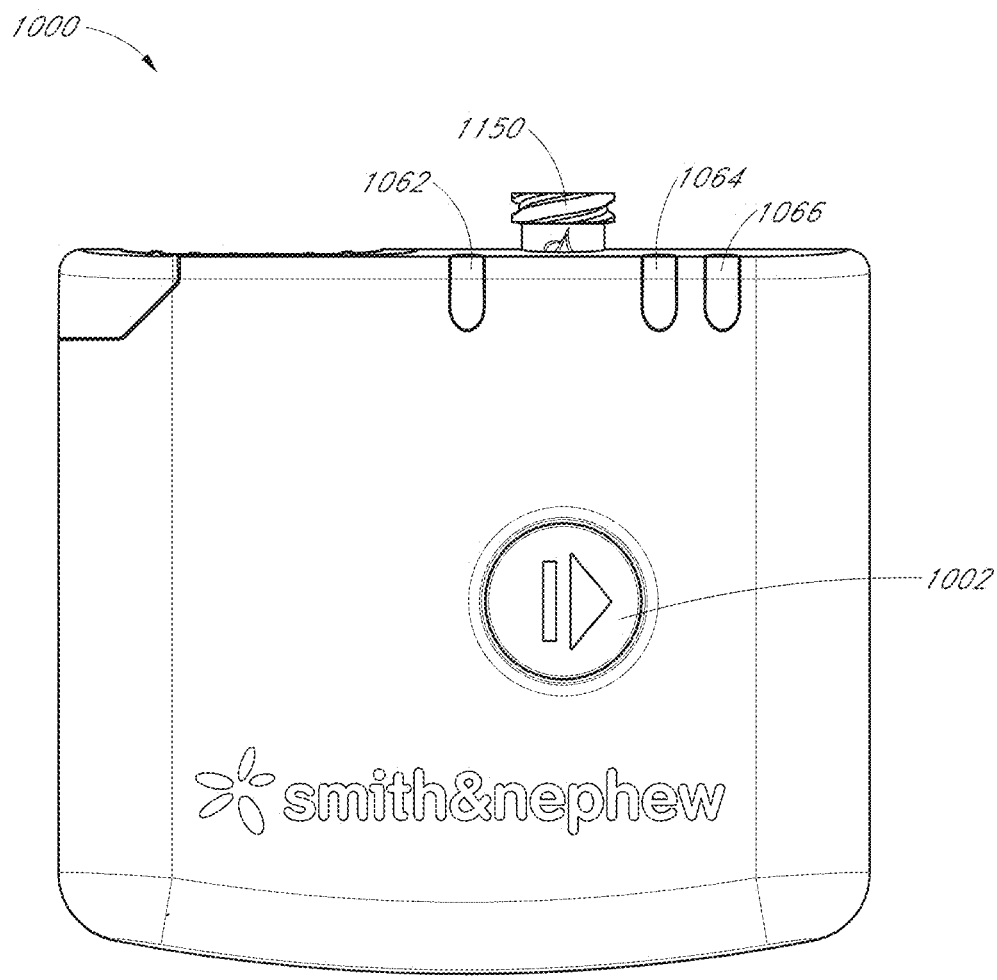
FIG. 5 illustrates a negative pressure wound therapy system according to some embodiments.

FIG. 5 illustrates a negative pressure wound therapy system 1000 according to some embodiments. Any of the embodiments of the negative pressure wound therapy system 1000 disclosed herein can have any one or more of the same or similar components, features, materials, sizes, configurations, and other details of any other system embodiments disclosed or incorporated by reference herein, including the embodiments of the pump assembly 310 in FIGS. 3A-B and the embodiments of the pump assembly 150 in FIGS. 1 and 4A-B. The negative pressure wound therapy system 1000 can be miniaturized and portable, although larger conventional portable or non-portable (e.g., wall suction) pumps can also be used. The negative pressure wound therapy system 1000 can include a switch or a button 1002, illustrated as a play/pause button located on the exterior of the housing of the system. The button 1002 can be configured to stop, pause, and/or restart negative pressure wound therapy. Although illustrated as a press button 1002, other types of switches or buttons can be included, such as a touchpad, touch screen, keyboard, and so on. The negative pressure wound therapy system 1000 can have one or more indicators, such as the three indicators 1062, 1064, 1066, for providing various indications as described herein. The one or more indicators can be visual indicators, such as one or more LEDs, audible, haptic, tactile, etc., or any combination of such indicators. The negative pressure wound therapy system 1000 can have one indicator, two indicators, or four or more indicators. The negative pressure wound therapy system 1000 can have a connector port or inlet 1150. The negative pressure wound therapy system 1000 can operate without a canister as described herein. In some cases, the illustrated negative pressure wound therapy system 1000 can be a PICO™ system sold by Smith & Nephew. Additional details regarding the negative pressure wound therapy system 1000 are described in U.S. Pat. Nos. 8,734,425, 8,905,985; and 9,901,664 each of which is incorporated by reference in its entirety.

Controlling Negative Pressure System and Detecting Blockages

Figure 6:
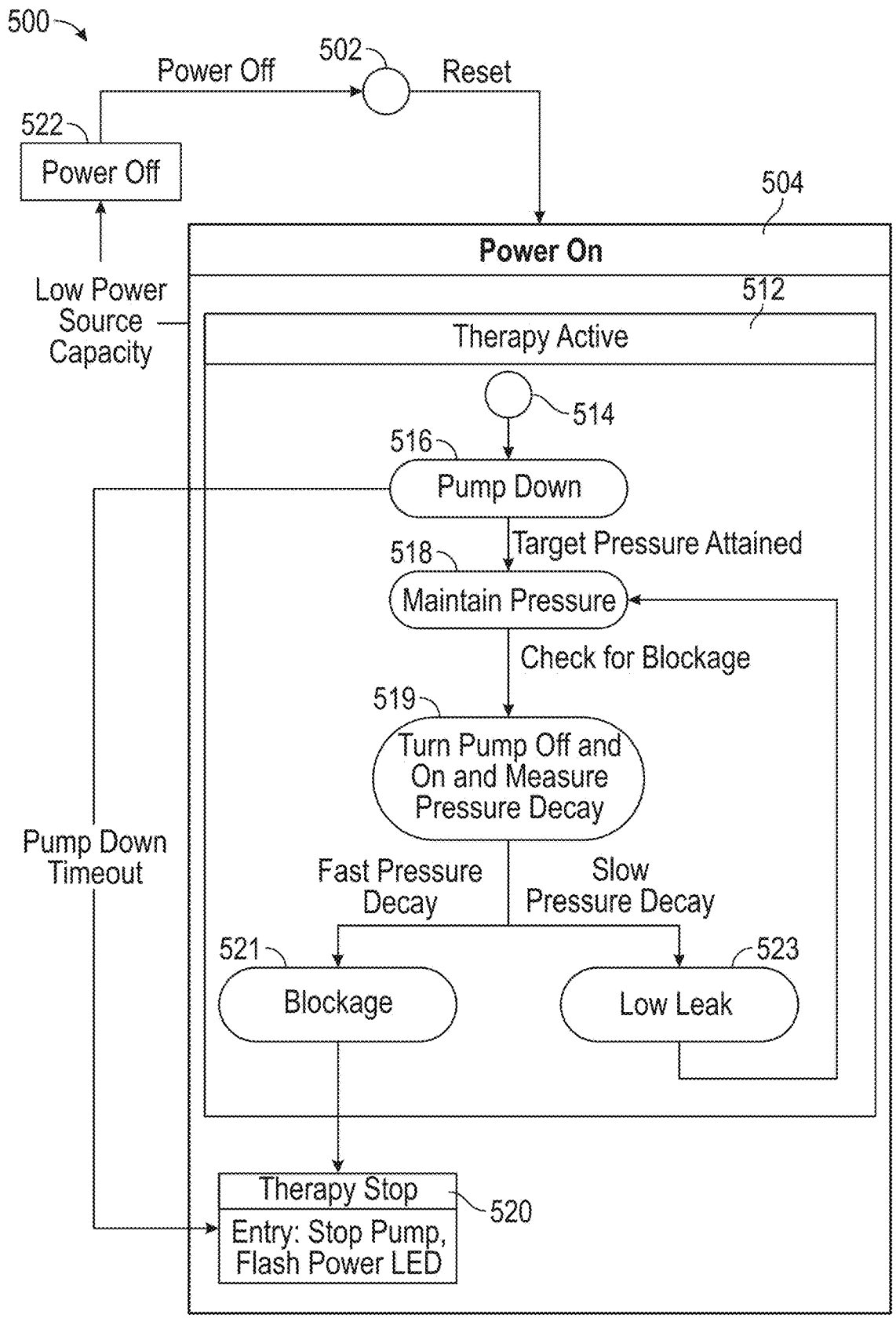
FIG. 6 illustrates a process for operating a negative pressure wound therapy system according to some embodiments.

FIG. 6 illustrates a process 500 for operating a negative pressure wound therapy system according to some embodiments. The process 500, which can also be referred to as a state machine, can be executed by one or more controllers of any of the systems, assemblies, or pumps disclosed herein, such as the system 100. The process 500 includes Power Off State 502, Power On States 504, and Power Off State 522. Power On States 504 can include Therapy Active States 512, and Therapy Stop State 520. The Therapy Active States 512 can further include Therapy Initialization State 514, Pump Down State 516, Maintain Pressure State 518, Turn Pump Off and On and Measure Pressure Decay State 519, Blockage State 521, and Low Leak State 523.

Operation of the TNP system can start in the Power Off State 502, and the process 500 can transition to the Power On States 504. This transition can be made automatically or in response to a user action, such as in response to a press of an "On" button (for example, one of the buttons 202). The process 500 can transition to the Power On States 504 from Power Off State 502 upon a system reset, which can be performed by the user through one or more of the buttons 202. Such system reset can involve a reset of the one or more controllers.

The process 500 can transition to the Power On States 504 in response to waking up from the Power Off State 522. In the Power Off State 522, the process 500 can be operating in low power mode, such as by causing the one or more processors to sleep or otherwise consume little power. This transition can be performed automatically, such as after passage of a duration of time. Alternatively or additionally, this transition can be performed in response to a user action as described herein. When the process 500 is in the Power Off State 522, the TNP system may be off and not provide negative pressure.

Upon transition to the Power On States 504, the process 500 can monitor or continue monitoring power source capacity, such as battery voltage or current. If the power source capacity falls below a certain threshold associated with proper operation of the TNP system, the process can transition to the Power Off State 522. The process 500 can transition from the Power On States 504 to the Power Off State 522 in response to a user action, such as in response to a press of an "Off" button (for example, one of the buttons 202). In some cases, a single button is configured to function as "On" and "Off" button.

Following a reset, timeout, or user action (such as, a button press), the process 500 can transition to the Therapy Active State 512. In some cases, Therapy Active States 512 are entered via the Therapy Initialization State 514. Upon transitioning to the Therapy Active States 512, the process 500 can determine that the TNP system is operating in canister or canisterless mode. For example, as described herein, the process can determine that the switch indicating attachment of a canister has been activated in order to determine that the TNP system is operating in the canister mode.

The process 500 can determine target pressure setpoint depending on the mode of operation. In some cases, in canisterless mode, the target pressure setpoint is preset. For example, the target pressure setpoint in canisterless mode can be −80 mmHg. In some cases, in canisterless mode, the target pressure setpoint can be selected. For example, the target pressure setpoint can be selected using the dial 316 as described herein. For instance, in canister mode, the target pressure setpoint can be selected as −60 mmHg, −80 mmHg, or −120 mmHg. In some cases, the target pressure setpoint can be set once by the process 500 before negative pressure therapy is applied and can remain set until the TNP system has been powered-off and on again.

The process 500 can transition to the Pump Down State 516 in which provision of negative pressure wound therapy is commenced. The process 500 can activate or start the negative pressure source to attempt to reduce pressure at the wound to the target pressure setpoint. The process 500 can monitor pressure at the wound with one or more pressure sensors positioned in a fluid flow path connecting the negative pressure source to the dressing. When the pressure has been successfully reduced to the target set point, the process 500 can transition to the Maintain Pressure State 518. In some cases, the process 500 can stop or deactivate the source of negative pressure when the target set point has been reached or attained. In some cases, the process 500 can slow down the source of negative pressure when the target set point has been reached or attained.

In the Maintain Pressure State 518, the target pressure can be maintained, for example, by activating the negative pressure source pump when pressure at the wound has decreased above the target pressure setpoint and deactivating the negative pressure source when the target pressure has been restored. Pressure at the wound can decrease above the setpoint (or become more positive) due to one or more leaks in the fluid flow path.

In both Pump Down State 516 and Maintain Pressure State 518, various system parameters, such as pressure at the wound, level of activity of the negative pressure source, or the like, can be monitored to determine whether negative pressure wound therapy should be stopped or additional or alternative indication should be provided. Such additional or alternative indication can include the process 500 providing one or more of visual (such as, using one or more indicators 204 as shown in FIGS. 2A and 2B), audible, haptic, tactile, or the like indications. Such determination can be based on finding of one or more blockages or leaks in the fluid flow path. In some cases, level of activity of the negative pressure source can be monitored via determining duty cycle of the negative pressure source, which can reflect proportion of time the negative pressure source is active over a time duration. In some cases, the level of activity of the negative pressure source can be monitored by one or more of power drawn (which can be determined by monitoring current or voltage), motor rotation, valve opening and closing, or the like. A timeout mechanism (such as, monitoring the blockage or the leak duration) or determination scheme using a hysteresis can be used to reduce a likelihood of false positives in the blockage or the leak detection.

In some cases, detection of a leak or blockage can cause the process 500 to transition into the Therapy Stop State 520 from one or more of Pump Down 516 or Blockage 521 States. In this state, negative pressure source can be stopped to pause provision of therapy. The process 500 can transition to the Therapy Stop State 520 in response to detecting: (1) pump down time indicative of a leak in canister or canisterless mode, (2) timeout indicative of blockage while maintaining pressure in the canister mode, (3) pressure decay due to a blockage, (4) timeout indicative of a leak while maintaining pressure in canister or canisterless mode, or the like.

The process 500 can distinguish between sustainable and unsustainable leaks or blockages as described herein. For example, a sustainable leak or blockage can be associated with less intense condition(s) that do not necessitate pausing or stopping therapy. Rather, the process 500 can indicate presence of the sustainable leak or blockage as described herein to permit the user to remedy the leak or blockage without the necessity to interrupt therapy. As another example, an unsustainable leak or blockage can be associated with more intense condition(s) that necessitate pausing or stopping therapy. Such unsustainable conditions can be so severe that continuing operation of the negative pressure source to provide therapy can drain the capacity of the power source.

When the target pressure setpoint cannot be reached in the Pump Down State 516 over a duration of time, the process 500 can determine presence of a leak. The process 500 can determine that such leak that prevents reaching the setpoint is unsustainable and indicate its presence by deactivating or stopping the negative pressure source. Additionally, the process 500 can indicate presence of the unsustainable leak visually, audibly, haptically, tactilely, or the like as described herein. Unsustainable leaks can be due to, for example, disconnecting the dressing from the negative pressure source when operating in the canisterless mode or disconnecting the canister when operating in the canister mode.

In some cases, the process 500 may not be able to restore the target pressure at the wound in the Maintain Pressure State 518 due to presence of a leak or blockage in the fluid flow path. The process 500 can distinguish between leak or blockage by comparing the level of activity of the negative pressure source, such as the duty cycle, to a leak threshold or blockage threshold as described herein. When blockage is present, fluid flow path volume through which the negative pressure source moves fluid is reduced. As a result, the level of activity of the negative pressure source decreases. When leak is present, fluid flow path volume through which the negative pressure source moves fluid is increased. As a result, the level of activity of the negative pressure source increases. By using different leak and blockage thresholds, the process 500 can distinguish between leak and blockage conditions. Leak and blockage thresholds can be selected or adjusted to account for canister or canisterless modes of operation. This can be advantageous because of different fluid flow path volumes when operating in both modes. For example, the fluid flow path volumes when operating in canister mode includes additional volume of the canister, which is not present in the canisterless mode.

The process 500 can monitor lifetime or usage time of the TNP system. For example, the process 500 can only update the lifetime in the Therapy Active States 512. Lifetime can be measured as total amount of time the negative pressure source has been active since initial activation of the TNP system. The process 500 can start measuring or monitoring lifetime only after a therapy has been successfully provided for a threshold period of time, such as 1 minute, 5 minutes, 10 minutes, 20 minutes, 25 minutes or the like. Successfully provision of therapy can correspond to being able to attain and maintain target pressure.

The process 500 can monitor the lifetime to determine when it the TNP system reaches end of life, such as 7 days of operation, 10 days of operation, 30 days of operation, or like. The process 500 can determine when the TNP system has reached or exceeded its expected therapy operation life or EOL. When the process 500 detects that EOL has been reached, ability of provide negative pressure wound therapy can be disabled. One or more of visual, audible, haptic, tactile, or the like indications can be provided as described herein.

Blockage Detection

Alternatively or additionally, the process 500 can determine or indicate presence of a blockage in the fluid flow path based on monitoring a pressure change in the fluid flow path. The negative pressure wound therapy system implementing the process 500 can be configured to provide negative pressure wound therapy even in a presence of a low leak, which can correspond to a low leak rate for gas entering the fluid flow path from the external environment (such as, the atmosphere). Such low leak condition can be due to presence of good seal(s) between the dressing and the wound as well as in other portion(s) of the fluid flow path. For example, the system 1000 illustrated in FIG. 5 can be configured to provide or maintain negative pressure wound therapy with a leak rate of less than approximately 0.1 mL/min at a target pressure setpoint of approximately −80 mmHg. As another example, the system 300 illustrated in FIG. 3 can be configured to provide or maintain negative pressure wound therapy in canisterless mode with a leak rate of less than approximately 0.15 mL/min at a target pressure setpoint of approximately −120 mmHg. As yet another example, the system 300 can be configured to provide or maintain negative pressure wound therapy in canister mode with a leak rate of less than approximately 50 scc/min (or standard cubic centimeters per minute) at a target pressure setpoint of approximately −60 mmHg. The preceding leak rates are provided for illustration and suitable smaller or larger leak rate values can be used depending on the embodiment.

Provision of negative pressure wound therapy in presence of a low leak in the fluid flow path or a blockage in the fluid flow path can be associated with a decreased level of activity of the negative pressure source. In case of a blockage, this decreased level of activity can be due to the reduction of the fluid flow path volume through which the negative pressure source moves fluid, which causes a slow flow through the fluid flow path. In case of the low leak, this decreased level of activity can be due to rather small amount of gas entering the fluid flow path, which likewise causes a slower flow of fluid that the negative pressure source moves through the fluid flow path.

To distinguish between these two operating conditions, the process 500 can monitor the pressure change in the fluid flow path. For example, the process 500 can activate or turn on the negative pressure source to aspirate fluid from the fluid flow path. If a blockage is present in the fluid flow path, the negative pressure source may be able to reduce pressure in the fluid flow path due to the evacuation of fluid (such as, gas) from the reduced volume in the fluid flow path downstream from the blockage. This reduced volume can include at least a portion of the conduit 140 that is downstream from the blockage. Such volume can be on the order of a few milliliters in some cases. The process 500 can monitor reduction in the pressure in the fluid flow path and determine or indicate presence of a blockage when the reduced pressure satisfies a value (such as, reaches a blockage threshold). If a blockage is not present in the fluid flow path, but, instead, the system is operating in the presence of a low leak in the fluid flow path, activation of the negative pressure source may not result in a discernable pressure reduction in the fluid flow path because the fluid flow path volume from which the negative pressure source evacuates fluid has not been reduced. This can be particularly so when a canister with a significant volume for storing removed fluids is present in the fluid flow path, such as during operation in canister mode as described herein.

Fluid flow path may not be perfectly sealed, and one or more small leaks can be present in the fluid flow path. For instance, one or more leaks can be present at or near location where a conduit connects to the pump assembly, such as at or near the connector 201 or the connector port 203. When a blockage is present, the reduced volume in the fluid flow path downstream from the blockage can depressurize when the negative pressure source is deactivated. For example, due to the one or more leaks, the reduced volume in the fluid flow path downstream from the blockage can attain atmospheric pressure when the negative pressure source is not active. Because of the reduced volume in the fluid flow path downstream from the blockage, such depressurization can occur rapidly. For example, if a canister filter is blocked (such as, due to the canister being full), volume of the fluid flow path downstream from the blockage can be very small because it may only include the conduit connecting the pump assembly to the canister. As another example, when the blockage is upstream from the canister (such as, in a conduit connecting the canister to the wound), volume of the fluid flow path downstream from the blockage can be slightly larger than in the previous example, but still be rather small. Depressurization when the negative pressure source is not active or negative pressure increase when the negative pressure source is activated can occur quite rapidly when one or more blockages are present in the fluid flow path.

For blockage detection, the process 500 can activate the negative pressure source for a short duration of time. For example, the process 500 can activate the negative pressure source for a period of time that is long enough to permit pressure in the fluid flow path to be reduced in case of a blockage, but short enough to not drain the capacity of the power source. For instance, the process 500 can activate the negative pressure source for 100 msec, less than 100 msec, or more than 100 msec. After the duration of time expires, the process 500 can deactivate or turn off the negative pressure source.

The process 500 can activate the negative pressure source for the duration of time suitable for detecting a blockage in the Turn Pump Off and On and Measure Pressure Decay State 519. The process 500 can transition to this state 519 from the Maintain Pressure State 518. For example, the process 500 can transition to the Turn Pump Off and On and Measure Pressure Decay State 519 after establishing (or reestablishing) the target pressure at the wound in the Maintain Pressure State 518. The process 500 can periodically transition to the Turn Pump Off and On and Measure Pressure Decay State 519. The duration of time during which the negative pressure source is active in the Turn Pump Off and On and Measure Pressure Decay State 519 can be shorter than a duration of time during which the negative pressure source is active in the Maintain Pressure State 518.

In the Turn Pump Off and On and Measure Pressure Decay State 519, the process 500 can activate the negative pressure source to determine a pressure change in the fluid flow path. The process 500 can determine a first pressure in the fluid flow path before the negative pressure source is activated in the Turn Pump Off and On and Measure Pressure Decay State 519. The process 500 can utilize a pressure sensor, as described herein. Prior to, at the time of, or after deactivating the negative pressure source in the Turn Pump Off and On and Measure Pressure Decay State 519, the process 500 can determine a second pressure in the fluid flow path. The process 500 can determine the pressure change or difference between the first and second pressures. The process 500 can compare the pressure difference to a value, such as a blockage threshold, to determine if a blockage is present in the fluid flow path. If the process 500 determines that the pressure difference satisfies the value (for instance, reaches or falls below the blockage threshold), the process 500 can transition to the Blockage State 521. In that state, the process 500 can indicate presence of blockage using any one or more indications described herein. The process 500 can additionally or alternatively deactivate the negative pressure source in the Blockage State 521. Provision of negative pressure can be restarted (for example, in the Pump Down State 516) following deactivation of the negative pressure source upon a timeout, user action (such as, a button press) or the like.

If the process 500 determines that the pressure difference does not satisfy the value (for instance, does not reach the blockage threshold), the process 500 can transition to the Low Leak State 523. In that state, the process 500 can indicate normal operation in presence of a low leak in the fluid flow path using any one or more indications described herein. The process 500 can remain in the Therapy Active 512 states. For example, the process 500 can transition to the Maintain Pressure State 518 from the Low Leak State 523.

The process 500 can execute the Turn Pump Off and On and Measure Pressure Decay State 519 a number of times prior to indicating presence of a blockage. Such detection can involve consecutive or non-consecutive executions of the State 519. The process 500 can transition to the Turn Pump Off and On and Measure Pressure Decay State 519 from any state other than the Maintain Pressure State 518 or any one or more states.

The process 500 can measure pressure change due to activation of the negative pressure source in the Maintain Pressure State 518 instead of doing so in the Turn Pump Off and On and Measure Pressure Decay State 519. In the Maintain Pressure State 518, the process 500 can determine the pressure change in the fluid flow path as a result of activation of the negative pressure source to restore the target pressure setpoint. As described herein, pressure change can be measured over the entire duration of activation of the negative pressure source or a portion such duration. The process can compare the determined pressure change to a value to indicate presence of a blockage as described herein.

The process 500 can measure pressure change due to activation of the negative pressure source in the Pump Down State 516 instead of doing so in the Turn Pump Off and On and Measure Pressure Decay State 519. The process 500 can indicate presence of a blockage as described herein.

Blockage detection based on monitoring pressure in the fluid flow path as described herein can quickly provide indication of any blockages present in the fluid flow path and allow the user to resolve such blockage quicker such that provision of therapy is not interrupted or interrupted for only a short duration of time.

Additional details regarding operating the negative pressure wound therapy system are described in U.S. Provisional Patent Application No. 62/664,688, filed on Apr. 30, 2018, and titled "SYSTEMS AND METHODS FOR CONTROLLING DUAL MODE NEGATIVE PRESSURE WOUND THERAPY APPARATUS", which is incorporated herein by reference in its entirety.

Terminology

Although some of the disclosed embodiments relate to a dual mode negative pressure wound therapy system, the approaches disclosed herein, including blockage detection, can be used in any negative pressure wound therapy system, such as a canister or canisterless system.

Many other variations than those described herein will be apparent from this disclosure. For example, depending on the embodiment, certain acts, events, or functions of any of the steps described herein can be performed in a different sequence, can be added, merged, or left out altogether (e.g., not all described acts or events are necessary for the practice of the processes). Moreover, in certain embodiments, acts or events can be performed concurrently. In addition, different tasks or processes can be performed by different machines and/or computing systems that can function together.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the described embodiments, and may be defined by claims as presented herein or as presented in the future.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations.

The scope of the present disclosure is not intended to be limited by the description of certain embodiments and may be defined by the claims. The language of the claims is to be interpreted broadly based on the language employed in the claims and not limited to the examples described in the present specification or during the prosecution of the application, which examples are to be construed as non-exclusive.

What is claimed is:

1. A method of operating a negative pressure wound therapy apparatus, the method comprising:
   activating a negative pressure source to attempt to reduce pressure in a fluid flow path connecting a wound covered by a wound dressing to the negative pressure source to approximately a negative pressure set point;
   deactivating the negative pressure source responsive to determining that pressure in the fluid flow path has been reduced to approximately the negative pressure set point;
   responsive to determining that pressure in the fluid flow path satisfies a threshold negative pressure that is more positive than the negative pressure set point, activating the negative pressure source for a first duration of time to reduce pressure in the fluid flow path to approximately the negative pressure set point; and
   responsive to determining that pressure in the fluid flow path has been reduced to approximately the negative pressure set point over the first duration of time:
      deactivating the negative pressure source;
      subsequently activating the negative pressure source for a second duration of time to attempt to reduce pressure in the fluid flow path, the second duration of time being shorter than the first duration of time;
determining a pressure change in the fluid flow path over at least part of the second duration of time;
deactivating the negative pressure source subsequent to expiration of the second duration of time; and
at a first time, responsive to determining that the pressure change in the fluid flow path over the at least part of the second duration of time indicates reduction in pressure, providing an indication of a blockage in the fluid flow path,
wherein the method is performed by a controller.

2. The method of claim 1, further comprising:
at a second time, responsive to determining that the pressure change in the fluid flow path over the at least part of the second duration of time does not indicate reduction in pressure, providing an indication of a leak in the fluid flow path.

3. The method of claim 1, further comprising:
at a second time, detecting a first leak in the fluid flow path that prevents reducing pressure in the fluid flow path to approximately the negative pressure set point; and
at a third time, detecting a second leak in the fluid flow path that does not prevent reducing pressure in the fluid flow path to approximately the negative pressure set point.

4. The method of claim 3, further comprising:
at a fourth time, responsive to determining that pressure in the fluid flow path has not been reduced to approximately the negative pressure set point, providing an indication of the first leak in the fluid flow path; and
at a fifth time, responsive to determining that the pressure change in the fluid flow path over the at least part of the second duration of time does not indicate reduction in pressure, providing an indication of the second leak in the fluid flow path.

5. The method of claim 4, wherein:
providing the indication of the first leak in the fluid flow path comprises deactivating the negative pressure source; and
providing the indication of the second leak in the fluid flow path does not comprise deactivating the negative pressure source.

6. The method of claim 1, wherein the second duration of time comprises of up to 100 milliseconds.

7. The method of claim 1, wherein pressure in the fluid flow path is reduced over the at least part of the second duration of time due to evacuation of gas from a portion of the fluid flow path downstream from the blockage.

8. The method of claim 7, wherein the fluid flow path includes a leak, and wherein the portion of the fluid flow path downstream from the blockage is depressurized over a duration of time when the negative pressure source is deactivated due to the leak.

9. The method of claim 1, wherein determining the pressure change in the fluid flow path over at least part of the second duration of time is performed based on a difference between a first pressure measurement made approximately at a start of the second duration of time and a second pressure measurement made approximately at an end of the second duration of time.

10. A method of operating a negative pressure wound therapy apparatus, the method comprising:
responsive to determining that pressure in a fluid flow path connecting a wound covered by a wound dressing and a negative pressure source satisfies a threshold negative pressure that is more positive than a negative pressure set point, activating the negative pressure source for a first duration of time to reduce pressure in the fluid flow path to approximately the negative pressure set point; and
responsive to determining that that pressure in the fluid flow path has been reduced to approximately the negative pressure set point over the first duration of time:
deactivating the negative pressure source;
subsequently activating the negative pressure source for a second duration of time to attempt to reduce pressure in the fluid flow path, the second duration of time being shorter than the first duration of time;
determining a pressure change in the fluid flow path over at least part of the second duration of time;
deactivating the negative pressure source subsequent to expiration of the second duration of time; and
at a first time, responsive to determining that the pressure change in the fluid flow path over the at least part of the second duration of time does not indicate reduction in pressure, providing an indication of a leak in the fluid flow path,
wherein the method is performed by a controller.

11. The method of claim 10, further comprising:
at a second time, responsive to determining that the pressure change in the fluid flow path over the at least part of the second duration of time indicates a reduction in pressure, providing an indication of a blockage in the fluid flow path.

12. The method of claim 11, wherein pressure in the fluid flow path is reduced over the at least part of the second duration of due to evacuation of gas from a portion of the fluid flow path downstream from the blockage.

13. The method of claim 12, wherein the portion of the fluid flow path downstream from the blockage is depressurized over a duration of time when the negative pressure source is deactivated.

14. The method of claim 10, further comprising:
at a second time, detecting and indicating a first leak in the fluid flow path that prevents reducing pressure in the fluid flow path to approximately the negative pressure set point; and
at a third time, detecting and indicating a second leak in the fluid flow path that does not prevent reducing pressure in the fluid flow path to approximately the negative pressure set point, the second leak being detected responsive to determining that the pressure change in the fluid flow path over the at least part of the second duration of time does not indicate reduction in pressure.

15. The method of claim 14, wherein:
indicating the first leak in the fluid flow path comprises deactivating the negative pressure source; and
indicating the second leak in the fluid flow path does not comprise deactivating the negative pressure source.

16. The method of claim 10, wherein the second duration of time comprises of up to 100 milliseconds.

17. The method of claim 10, wherein determining the pressure change in the fluid flow path over at least part of the second duration of time is performed based on a difference between a first pressure measurement made approximately at a start of the second duration of time and a second pressure measurement made approximately at an end of the second duration of time.

* * * * *

UNITED STATES PATENT AND TRADEMARK OFFICE
CERTIFICATE OF CORRECTION

PATENT NO. : 12,029,842 B2
APPLICATION NO. : 18/224454
DATED : July 9, 2024
INVENTOR(S) : Ben Alan Askem It is certified that error appears in the above-identified patent and that said Letters Patent is hereby corrected as shown below:

On the Title Page

Column 2 (Abstract), Line 5, delete "ae" and insert -- a --.

In the Specification

Column 7, Line 6, delete "Renays" and insert -- Renasys --.

Column 8, Line 60, delete "can by" and insert -- can be --.

In the Claims

Column 22, Line 7, Claim 10, delete "that that" and insert -- that --.

Signed and Sealed this
Twenty-first Day of January, 2025

Coke Morgan Stewart
*Acting Director of the United States Patent and Trademark Office*